United States Patent
Lai et al.

(10) Patent No.: US 9,459,536 B1
(45) Date of Patent: Oct. 4, 2016

(54) NEGATIVE TONE DEVELOPER COMPOSITION FOR EXTREME ULTRAVIOLET LITHOGRAPHY

(71) Applicant: Taiwan Semiconductor Manufacturing Company, Ltd., Hsin-Chu (TW)

(72) Inventors: Wei-Han Lai, Taipei (TW); Ching-Yu Chang, Hsin-Chu (TW)

(73) Assignee: TAIWAN SEMICONDUCTOR MANUFACTURING COMPANY, LTD., Hsin-Chu (TW)

(*) Notice: Subject to any disclaimer, the term of this patent is extended or adjusted under 35 U.S.C. 154(b) by 0 days.

(21) Appl. No.: 14/755,049

(22) Filed: Jun. 30, 2015

(51) Int. Cl.
| | |
|---|---|
| G03F 7/32 | (2006.01) |
| G03F 7/20 | (2006.01) |
| H01L 21/027 | (2006.01) |
| H01L 21/033 | (2006.01) |
| C07C 69/12 | (2006.01) |
| C07C 69/22 | (2006.01) |
| C07C 69/62 | (2006.01) |
| C07C 69/63 | (2006.01) |

(52) U.S. Cl.
CPC ............. *G03F 7/325* (2013.01); *C07C 69/12* (2013.01); *C07C 69/22* (2013.01); *C07C 69/62* (2013.01); *C07C 69/63* (2013.01); *G03F 7/20* (2013.01); *H01L 21/0274* (2013.01); *H01L 21/0337* (2013.01)

(58) Field of Classification Search
CPC ... G03F 7/325; G03F 7/039; H01L 21/0274; H01L 21/0337; C07C 69/00; C07C 69/62; C07C 69/63; C07C 69/12; C07C 69/22
USPC .............. 430/270.1, 322, 434, 435; 560/219, 560/227, 105
See application file for complete search history.

(56) References Cited

U.S. PATENT DOCUMENTS

| | | | | |
|---|---|---|---|---|
| 3,384,628 A | * | 5/1968 | Pittman ................... | C07C 29/68 442/80 |
| 5,466,899 A | * | 11/1995 | Geisenberger .......... | F01N 1/065 181/206 |
| 5,898,046 A | * | 4/1999 | Raiford .................... | C08K 5/06 524/316 |
| 6,063,474 A | * | 5/2000 | Raiford .................... | C08K 5/06 428/357 |

(Continued)

FOREIGN PATENT DOCUMENTS

JP      2001-318472 A   * 11/2001         7/325

OTHER PUBLICATIONS

Machine translation of JP 2001-318472 (no date).*

(Continued)

*Primary Examiner* — Amanda C Walke
(74) *Attorney, Agent, or Firm* — Haynes and Boone, LLP

(57) ABSTRACT

A method for lithography patterning includes providing a substrate; forming a material layer over the substrate; exposing a portion of the material layer to a radiation; and removing an unexposed portion of the material layer in a developer, resulting in a patterned material layer. The developer has a Log P value greater than 1.82 and contains an organic solvent. In an embodiment, the organic solvent is an n-butyl acetate derivative that is represented by the formula $CH_3R_5CHR_4CHR_3CHR_2COOCH_2R_1$, wherein $R_1$, $R_2$, $R_3$, $R_4$, and $R_5$ are each selected from a group consisting of hydrogen, a methyl group, an ethyl group, and a fluoroalkyl group.

20 Claims, 5 Drawing Sheets

(56) References Cited

U.S. PATENT DOCUMENTS

| | | | | |
|---|---|---|---|---|
| 7,034,179 B2* | 4/2006 | Okazoe | ............... | C07C 41/06 560/219 |
| 7,161,025 B2* | 1/2007 | Okazoe | ............... | C07C 41/06 560/227 |
| 8,017,304 B2 | 9/2011 | Tarutani et al. | | |
| 8,980,108 B1 | 3/2015 | Yu et al. | | |
| 2008/0305401 A1* | 12/2008 | Smart | ............... | H01M 4/505 429/326 |
| 2015/0008211 A1* | 1/2015 | Takano | ............... | G03F 7/039 216/11 |
| 2015/0147649 A1* | 5/2015 | Jung | ............... | H01M 4/366 429/220 |

OTHER PUBLICATIONS

U.S. Appl. No. 14/498,389, filed Sep. 26, 2014, by inventors Chen-Yu Liu and Ching-Yu Chang for "Cleaning Composition and Method for Semiconductor Device Fabrication," 18 pages of text, 9 pages of drawings.

U.S. Appl. No. 14/529,944, filed Oct. 31, 2014, by inventors Chang Lilin and Ching-Yu Chang for "Lithography Patterning Technique," 20 pages of text, 4 pages of drawings.

* cited by examiner

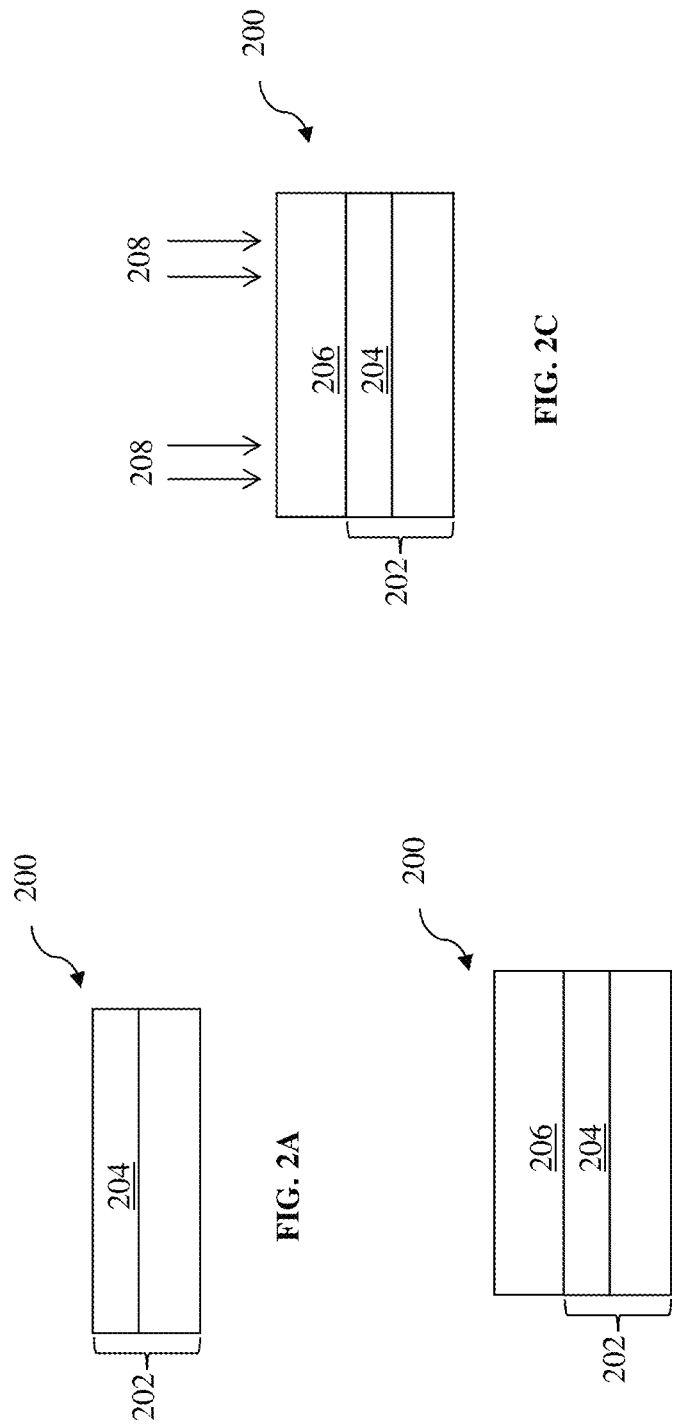

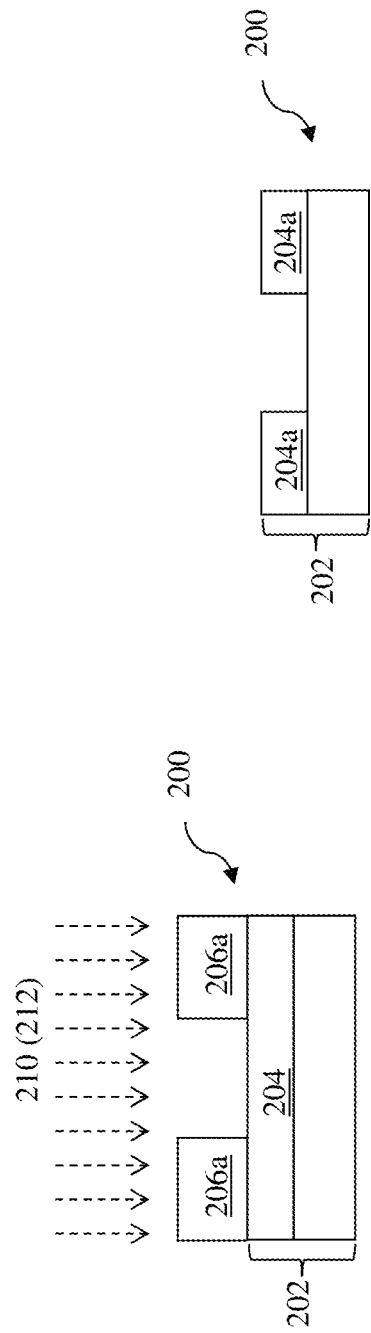

NEGATIVE TONE DEVELOPER COMPOSITION FOR EXTREME ULTRAVIOLET LITHOGRAPHY

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component (or line) that can be created using a fabrication process) has decreased. This scaling down process generally provides benefits by increasing production efficiency and lowering associated costs. Such scaling down has also increased the complexity of processing and manufacturing ICs.

For example, extreme ultraviolet (EUV) lithography has been utilized to support critical dimension (CD) requirements of smaller devices. EUV lithography employs scanners using radiation in the EUV region, having a wavelength of about 1-100 nm. Some EUV scanners provide 4× reduction projection printing onto a resist film coated on a substrate, similar to some optical scanners, except that the EUV scanners use reflective rather than refractive optics. EUV lithography has imposed a complex set of requirements upon the resist film. Many variations of chemically amplified resist have been explored, among which Polyhydroxystyrene (PHS) resist exhibits very desirable properties for EUV lithography. However, there are various issues associated with developing the PHS resist in present negative tone developers, which cause increased line edge roughness (LER), line width roughness (LWR), and pattern deformation.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

FIGS. 2A, 2B, 2C, 2D, and 2E illustrate cross sectional views of forming a target pattern according to the method of FIG. 1, in accordance with an embodiment.

DETAILED DESCRIPTION

Figure 1:
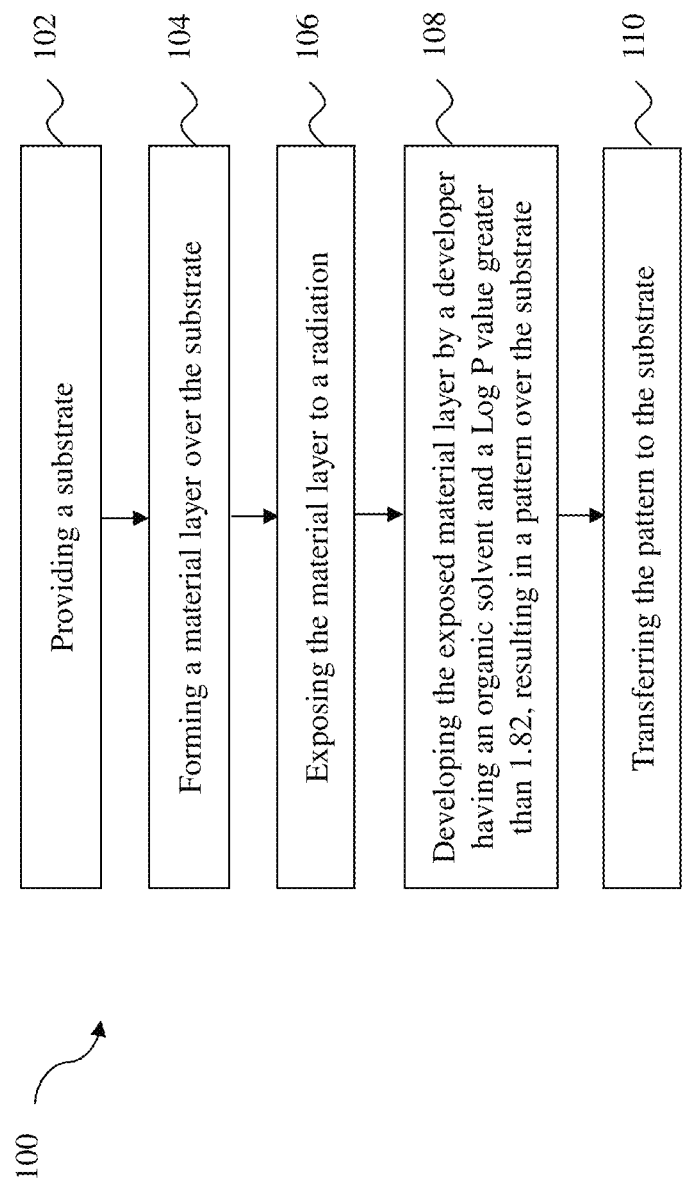
FIG. 1 illustrates a flow chart of a lithography patterning method according to various aspects of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The present disclosure is generally related to methods for semiconductor device fabrication, and more particularly to compositions for developing exposed resist films in extreme ultraviolet (EUV) lithography and methods of using the same. In lithography patterning, after a resist film is exposed to a radiation, such as a EUV radiation or an electron beam (e-beam), it is developed in a developer (a chemical solution). The developer removes portions of the resist film, thereby forming a resist pattern which may include line patterns and/or trench patterns. The resist pattern is then used as an etch mask in subsequent etching processes, transferring the pattern to underlying patterning layers.

There are generally two types of processes for developing exposed resist films: a positive tone development (PTD) process and a negative tone development (NTD) process. The PTD process uses a PTD developer. The NTD process uses a NTD developer. The term "PTD developer" as used herein indicates a developer that selectively dissolves and removes the exposed areas of a resist film not lower than a first predetermined threshold value. The term "NTD developer" as used herein indicates a developer that selectively dissolves and removes the unexposed areas of a resist film as well as the under-exposed areas of the resist film, i.e., the areas exposed not higher than a second predetermined threshold value. The first and second threshold values may be the same or different, depending on the parameters of the resist material and the developer. In the following disclosure, the term "unexposed area" of a resist film (or a resist layer) includes both unexposed and under-exposed areas of the resist film.

In present EUV lithography, NTD processes provide better optical performance for sub-10 nanometer (nm) fabrication than PTD processes. One of the resists used for EUV NTD processes is Polyhydroxystyrene (PHS) resist. It has great potential for applications in EUV lithography due to its sensitivity to EUV wavelength and ability to stably generate secondary electrons. However, commonly used NTD developers, such as n-butyl acetate (n-BA), dissolve the PHS resist easily and can penetrate the PHS resist even after it has been exposed with EUV radiations. This generally results in resist pattern swelling problems, causing increased line edge roughness (LER), line width roughness (LWR), and even pattern deformation. An object of the present disclosure is to provide a new and improved NTD developer that can develop a resist, such as a resist containing PHS, while achieving high pattern fidelity in advanced lithography processes including EUV lithography and e-beam lithography.

FIG. 1 is a flow chart of a method 100 of patterning a substrate (e.g., a semiconductor wafer) according to various aspects of the present disclosure. The method 100 may be implemented, in whole or in part, by a system employing deep ultraviolet (DUV) lithography, extreme ultraviolet (EUV) lithography, electron beam (e-beam) lithography, x-ray lithography, and other lithography processes to improve pattern dimension accuracy. In the present embodiment, EUV lithography is used as the primary example. Additional operations can be provided before, during, and after the method 100, and some operations described can be replaced, eliminated, or moved around for additional embodiments of the method. The method 100 is an example, and is not intended to limit the present disclosure beyond what is explicitly recited in the claims. The method 100 is described below in conjunction with FIGS. 2A-2E wherein a semiconductor device 200 is fabricated by using embodiments of the method 100. The semiconductor device 200 may be an intermediate device fabricated during processing of an IC, or a portion thereof, that may comprise SRAM and/or other logic circuits, passive components such as resistors, capacitors, and inductors, and active components such as p-type FETs (PFETs), n-type FETs (NFETs), fin-like FETs (FinFETs), other three-dimensional (3D) FETs, metal-oxide semiconductor field effect transistors (MOSFET), complementary metal-oxide semiconductor (CMOS) transistors, bipolar transistors, high voltage transistors, high frequency transistors, other memory cells, and combinations thereof.

The method 100 (FIG. 1) is provided with a substrate 202 (FIG. 2A) at operation 102. Referring to FIG. 2A, the substrate 202 includes one or more layers of material or composition. In an embodiment, the substrate 202 is a semiconductor substrate (e.g., wafer). In another embodiment, the substrate 202 includes silicon in a crystalline structure. In alternative embodiments, the substrate 202 includes other elementary semiconductors such as germanium, or a compound semiconductor such as silicon carbide, gallium arsenide, indium arsenide, and indium phosphide. The substrate 202 may include a silicon on insulator (SOI) substrate, be strained/stressed for performance enhancement, include epitaxial regions, include isolation regions, include doped regions, include one or more semiconductor devices or portions thereof, include conductive and/or non-conductive layers, and/or include other suitable features and layers. In the present embodiment, the substrate 202 includes a patterning layer 204. In an embodiment, the patterning layer 204 is a hard mask layer including material(s) such as amorphous silicon (a-Si), silicon oxide, silicon nitride (SiN), titanium nitride, or other suitable material or composition. In an embodiment, the patterning layer 204 is an anti-reflection coating (ARC) layer such as a nitrogen-free anti-reflection coating (NFARC) layer including material(s) such as silicon oxide, silicon oxygen carbide, or plasma enhanced chemical vapor deposited silicon oxide. In various embodiments, the patterning layer 204 may include a high-k dielectric layer, a gate layer, a hard mask layer, an interfacial layer, a capping layer, a diffusion/barrier layer, a dielectric layer, a conductive layer, other suitable layers, and/or combinations thereof. In another embodiment, the substrate 202 is a mask substrate that may include a low thermal expansion material such as quartz, silicon, silicon carbide, or silicon oxide-titanium oxide compound. To further this example, the substrate 202 may be a mask substrate for making a deep ultraviolet (DUV) mask, an extreme ultraviolet (EUV) mask, or other types of masks.

The method 100 (FIG. 1) proceeds to operations 104 by forming a material layer 206 over the substrate 202 (FIG. 2B). Referring to FIG. 2B, in an embodiment, the material layer 206 is formed by spin-on coating a liquid polymeric material onto the substrate 202. In an embodiment, the material layer 206 is further treated with a soft baking process and a hard baking process. In an embodiment, the material layer 206 is a radiation sensitive layer, such as a photoresist including an I-line resist, a DUV resist including a krypton fluoride (KrF) resist and argon fluoride (ArF) resist, a EUV resist, an electron beam (e-beam) resist, and an ion beam resist. In the present embodiment, the material layer 206 is a resist sensitive to EUV radiation and is further for NTD development, i.e., its solubility in a NTD developer decreases upon EUV radiation. In an embodiment, the material layer 206 contains PHS resist. For example, the material layer 206 may contain more than 0% but less than 40% PHS resist. To further this embodiment, the PHS resist may be a part of a copolymer in the material layer 206, or may be blended with another polymer to form the material layer 206. For the sake of convenience, the material layer 206 is simply referred to as the resist film (or resist) 206 in the following discussion. In an embodiment, the resist film 206 contains photo-acid generators (PAGs) which, upon radiation, produce an acid. To further this embodiment, the resist film 206 may contain about 5% PAGs.

The method 100 (FIG. 1) proceeds to operation 106 by exposing the resist film 206 to a radiation beam 208 in a lithography system. Referring to FIG. 2C, the radiation beam 208 may be an I-line (365 nm), a DUV radiation such as KrF excimer laser (248 nm) or ArF excimer laser (193 nm), a EUV radiation (e.g., 13.8 nm), an e-beam, an x-ray, an ion beam, or other suitable radiations. Operation 106 may be performed in air, in a liquid (immersion lithography), or in a vacuum (e.g., for EUV lithography and e-beam lithography). In an embodiment, the radiation beam 208 is patterned with a mask, such as a transmissive mask or a reflective mask, which may include resolution enhancement techniques such as phase-shifting and/or optical proximity correction (OPC). In another embodiment, the radiation beam 208 is directly modulated with a predefined pattern, such as an IC layout, without using a mask (maskless lithography). In the present embodiment, the radiation beam 208 is a EUV radiation and the operation 106 is performed in a EUV lithography system, such as the EUV lithography system 300 shown in FIG. 3.

Figure 3:
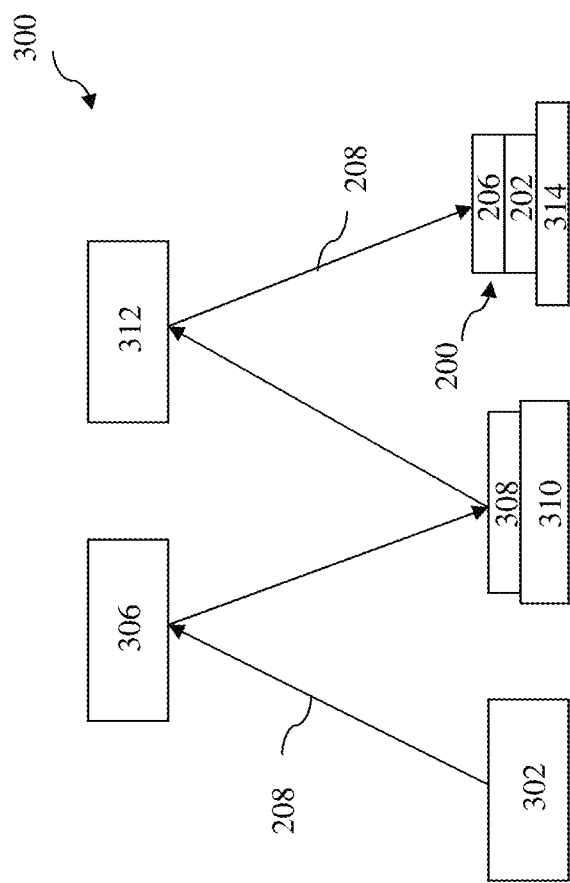
FIGS. 3 and 4 illustrate apparatuses that may be employed by the method of FIG. 1, in accordance with some embodiments.

Referring to FIG. 3, the EUV lithography system 300 includes a radiation source 302 that produces the radiation beam 208, condenser optics 306, a mask stage 310 securing a mask 308 thereon, projection optics 312, and a substrate stage 314 securing the device 200 including the substrate 202 and the resist film 206. Other configurations and inclusion or omission of items may be possible. In the present disclosure, the EUV lithography system 300 may be a stepper or a scanner.

The radiation source 302 provides the radiation beam 208 having a wavelength in the EUV range, such as about 1-100 nm. In an embodiment, the radiation beam 208 has a wavelength of about 13.5 nm. The condenser optics 306 includes a multilayer coated collector and a plurality of grazing mirrors. The condenser optics 306 is configured to collect and shape the radiation beam 208 and to provide a slit of the radiation beam 208 to the mask 308. The mask 308, also referred to as a photomask or a reticle, includes patterns of one or more target IC devices. The mask 308 provides a patterned aerial image to the radiation beam 208. The mask 308 is a reflective mask in the present embodiment, and may incorporate resolution enhancement techniques such as phase-shifting techniques and/or optical proximity correction (OPC). The mask stage 310 secures the mask 308 thereon, such as by vacuum, and provides accurate position and movement of the mask 308 during alignment, focus, leveling and exposure operation in the EUV lithography system 300.

The projection optics 312 includes one or more lens and a plurality of mirrors. The lens may have a magnification of less than one thereby reducing the patterned aerial image of the mask 308 to the device 200, particularly, to the resist film 206. The device 200 is secured by the substrate stage 314 which provides accurate position and movement of the device 200 during alignment, focus, leveling and exposing operation in the EUV lithography system 300 such that the patterned aerial image of the mask 308 is exposed onto the resist film 206 in a repetitive fashion (though other lithography methods are possible). The irradiated portions of the resist film 206 become insoluble in a NTD developer. In an embodiment where the resist film 206 contains PAGs, the semiconductor device 200 may be subjected to one or more post-exposure baking processes, which accelerate the resist pattern formation process.

The method 100 (FIG. 1) proceeds to operation 108 by developing the exposed resist film 206 in a developer 210, constructed according to various aspects of the present disclosure. In the present embodiment, the developer 210 is a NTD developer that dissolves and removes unexposed portions of the resist film 206, resulting a resist pattern 206a (FIG. 2D). In the example as shown in FIG. 2D, the resist pattern 206a are represented by two line patterns. However, the following discussion is equally applicable to resist patterns represented by trenches.

As discussed above, a commonly used NTD developer, n-butyl acetate (n-BA), does not suit EUV lithography very well, partly because it dissolves PHS resist easily and may even penetrate exposed areas of a PHS resist, resulting in increased line edge roughness and even pattern deformation. The Applicants have discovered new and improved NTD developer compositions that provide superior performance in EUV lithography than n-BA. The NTD developer 210 is an embodiment of the new and improved developer compositions. In an embodiment, the NTD developer 210 includes an organic solvent 212 and has a Log P value greater than 1.82. The organic solvent 212 may be an n-BA derivative. In various embodiments, the organic solvent 212 is represented by the formula (I) below:

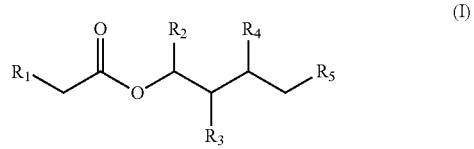

(I)

In the above formula (I), $R_1$, $R_2$, $R_3$, $R_4$, and $R_5$ are each selected from a group consisting of hydrogen, a methyl group, an ethyl group, and a fluoroalkyl group.

In an embodiment, the organic solvent 212 is represented by the formula (I), and further, each of $R_1$, $R_2$, $R_3$, $R_4$, and $R_5$ is a methyl group. Some exemplary formulae of this embodiment are shown below in (II-A) through (II-E):

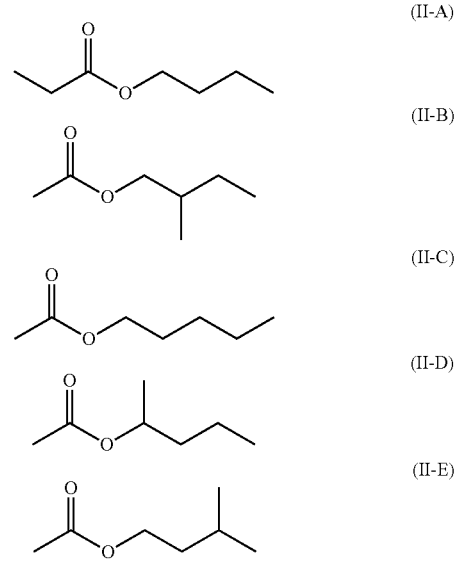

In an embodiment, the organic solvent 212 is represented the formula (I), and further, each of $R_1$, $R_2$, $R_3$, $R_4$, and $R_5$ is an ethyl group. Some exemplary formulae of this embodiment are shown below in (III-A) through (III-E):

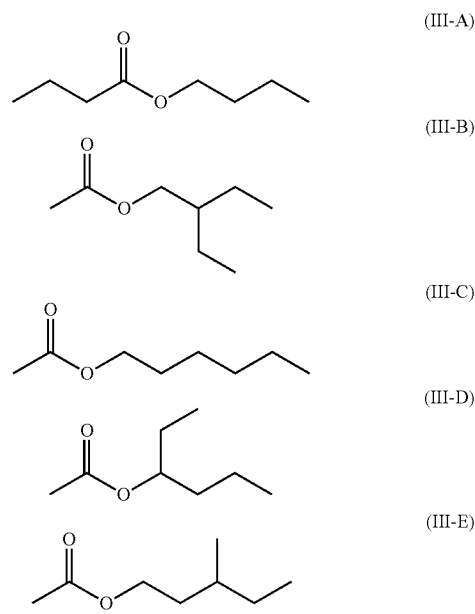

In an embodiment, the organic solvent 212 is represented by the formula (I), and further, each of $R_1$, $R_2$, $R_3$, $R_4$, and $R_5$ is a fluoroalkyl group having $CF_3$. Some exemplary formulae of this embodiment are shown below in (IV-A) through (IV-E):

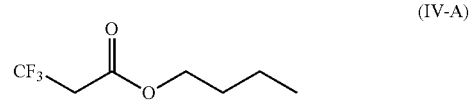

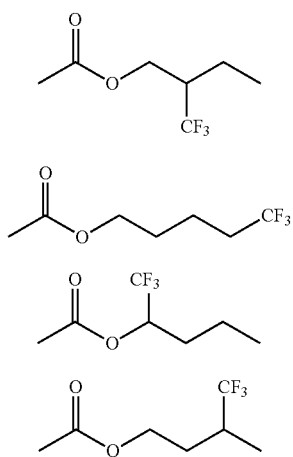

In an embodiment, the organic solvent 212 is represented by the formula (I), and further, each of $R_1$, $R_2$, $R_3$, $R_4$, and $R_5$ is a fluoroalkyl group having $C_2F_5$. Some exemplary formulae of this embodiment are shown below in (V-A) through (V-E):

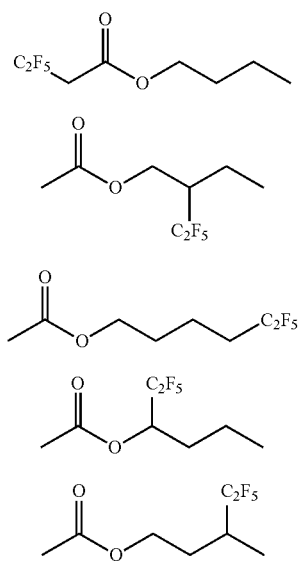

In various embodiments, the developer 210 may further include low molecular additives and surfactants. In some embodiments, the developer 210 may further include n-butyl acetate (n-BA) as a co-solvent. The ratio between the organic solvent 212 and the co-solvent n-BA may be determined by the characteristics of the resist film 206, such as the solubility, the molecular weights, the molecular weight dispersity, the polarity of monomers, the monomer sequences, etc.

Still referring to FIG. 2D, the developer 210, constructed according to various aspects of the present disclosure, is applied to the resist film 206. The unexposed portions (including under-exposed portions) of the resist film 206 are dissolved by the developer 210, leaving the exposed portion 206a as the resist pattern over the substrate 202. Due to the properties of the developer 210 discussed above, the resist pattern 206a has very smooth edges and sidewalls, therefore low LER and LWR.

Figure 4:
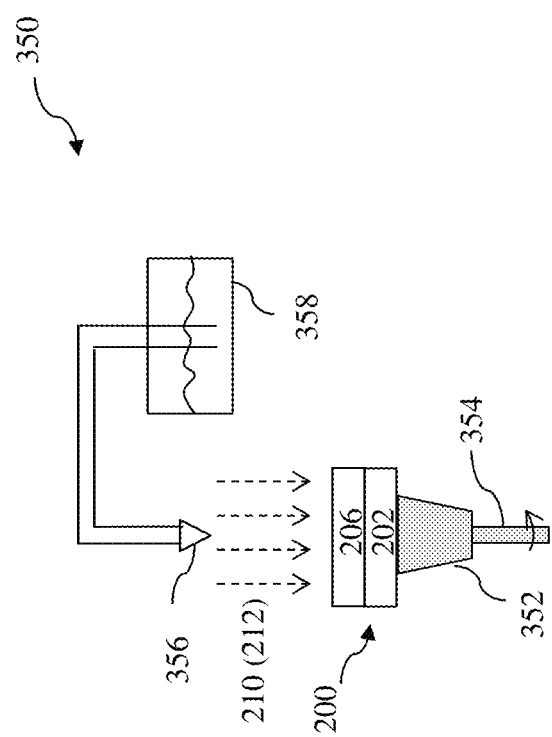

In embodiments, the developer 210 is applied to the device 200 in a developing tool 350. An exemplary developing tool 350 is shown, in portion, in FIG. 4. Referring to FIG. 4, the developing tool 350 is part of a cluster tool in a semiconductor fabrication process. After the resist film 206 has been exposed in the EUV lithography system 300, the device 200 is transferred to the developing tool 350 which applies the developer 210 to the resist film 206. In the embodiment as shown, the developing tool 350 applies the developer 210 in a spin-on process, i.e., it sprays the developer 210 onto the resist film 206 while spinning the device 200.

As shown in FIG. 4, the developing tool 350 includes a substrate stage 352 designed to secure the device 200 including the resist film 206. The substrate stage 352 is operable to spin such that the device 200 secured thereon is spun accordingly during the spin-on developing process. The substrate stage 352 includes a mechanism, such as vacuum suction mechanism, e-chucking, or other suitable mechanism, to secure the device 200. The developing tool 350 further includes a motion mechanism 354 integrated with the substrate stage 352 and is operable to drive the substrate stage 352 and the device 200 secured thereon in various motion modes. In some embodiments, the motion mechanism 354 includes a motor to drive the substrate stage 352 and the device 200 to spin at a certain spin speed during various operations (such as developing and rinsing). In some embodiments, the motion mechanism 354 includes an elevation module to move the device 200 along a vertical direction so that the device 200 is able to be positioned at a lower or higher level.

The developer 210 is dispensed through a nozzle 356 over the device 200 while it is spun. The developer 210 is stored in a container 358 and is delivered to the nozzle 356 through a delivery apparatus that includes a pipeline. The developer 210 may be delivered using a pump, a pressurized gas, or other mechanisms. In an embodiment, the developer 210 includes n-BA as a co-solvent. To further this embodiment, the organic solvent 212 and the co-solvent n-BA may be pre-mixed and stored in the container 358. Alternatively, the organic solvent 212 and the co-solvent n-BA may be stored in separate containers (similar to the container 358) and are mixed through the delivery apparatus up to the nozzle 356 while the developer 210 is being applied. In various embodiments, the developing tool 350 can control the mixing ratio between the organic solvent 212 and the co-solvent n-BA, which may depend on various physical values related to the parameters of the resist film 206. For example, the mixing recipe may take into account the characteristics of the polymer in the resist film 206, the average molecular weight, the molecular weight dispersity, the polarity and sequences of the monomers, etc.

In various embodiments, the developer 210 can be continuously sprayed onto the device 200. Alternatively, it can be applied by other means such as a puddle process. The method 100 may include further operations to finalize the resist pattern 206a after the operation 108. For example, the device 200 may be subjected to a rinsing operation using de-ionized (DI) water to remove residues and particles, and/or a post-development baking (PDB) process to harden the resist pattern 206a so as to increase its structural stability.

The method 100 (FIG. 1) proceeds to operation 110 to etch the substrate 202 using the resist pattern 206a as an etch mask, thereby transferring the pattern from the resist pattern 206a to the substrate 202 (FIG. 2E). In an embodiment, the patterning layer 204 is a hard mask layer. To further this embodiment, the pattern is first transferred from the resist pattern 206a to the hard mask layer 204, then to other layers of the substrate 202. For example, the hard mask layer 204 may be etched through openings of the resist pattern 206a using a dry (plasma) etching, a wet etching, and/or other etching methods. For example, a dry etching process may implement an oxygen-containing gas, a fluorine-containing gas (e.g., $CF_4$, $SF_6$, $CH_2F_2$, $CHF_3$, and/or $C_2F_6$), a chlorine-containing gas (e.g., $Cl_2$, $CHCl_3$, $CCl_4$, and/or $BCl_3$), a bromine-containing gas (e.g., HBr and/or $CHBR_3$), an iodine-containing gas, other suitable gases and/or plasmas, and/or combinations thereof. The resist pattern 206a may be partially or completely consumed during the etching of the hard mask layer 204. In an embodiment, any remaining portion of the resist pattern 206a may be stripped off, leaving a patterned hard mask layer 204a over the substrate 202, as illustrated in FIG. 2E.

Although not shown in FIG. 1, the method 100 may proceed to forming a final pattern or an IC device on the substrate 202. In an embodiment, the substrate 202 is a semiconductor substrate and the method 100 proceeds to forming fin field effect transistor (FinFET) structures. In this embodiment, operation 110 forms a plurality of active fins in the semiconductor substrate 202. The active fins have uniform CD, due to the low LER and LWR of the resist pattern 206a. In another embodiment, the method 100 proceeds to forming a plurality of gate electrodes in the semiconductor substrate 202. The gate electrodes have uniform gate length due to the resist pattern 206a's smooth sidewalls. The method 100 may further form gate spacers, doped source/drain regions, contacts for gate/source/drain features, etc. In another embodiment, a target pattern is to be formed as metal lines in a multilayer interconnection structure. For example, the metal lines may be formed in an inter-layer dielectric (ILD) layer of the substrate 202, which has been etched by operation 110 to include a plurality of trenches. The method 100 proceeds to filling the trenches with a conductive material, such as a metal; and polishing the conductive material using a process such as chemical mechanical planarization (CMP) to expose the patterned ILD layer, thereby forming the metal lines in the ILD layer. The above are non-limiting examples of devices/structures that can be made and/or improved using the method 100 and the developer 210 according to various aspects of the present disclosure.

Although not intended to be limiting, one or more embodiments of the present disclosure provide many benefits to a semiconductor device and the formation thereof. For example, a resist developer constructed according to the present disclosure provides superior performance in NTD processes for advanced lithography, such as EUV lithography or e-beam lithography. Embodiments of this developer are suitable for developing a resist film containing PHS. Using such developer leads to reduced resist pattern swelling, and reduced resist pattern surface roughness such as line edge roughness (LER) and/or line width roughness (LWR). Such resist developer is advantageous in nanometer semiconductor fabrication where critical dimension (CD) uniformity has become a critical factor in circuit performance.

In one exemplary aspect, the present disclosure is directed to a method for lithography patterning. The method includes providing a substrate; forming a material layer over the substrate; exposing a portion of the material layer to a radiation; and removing an unexposed portion of the material layer in a developer, resulting in a patterned material layer, wherein the developer contains an organic solvent and has a Log P value greater than 1.82.

In another exemplary aspect, the present disclosure is directed to a method for lithography patterning. The method includes forming a resist layer over a substrate; exposing a portion of the resist layer to an EUV radiation; and removing an unexposed portion of the resist layer in a developer, resulting in a patterned resist layer, wherein the developer has a Log P value greater than 1.82 and contains a solvent that is an n-butyl acetate (n-BA) derivative.

In another exemplary aspect, the present disclosure is directed to a lithography developing composition with a Log P value greater than 1.82. The composition includes an organic solvent that is represented by the formula:

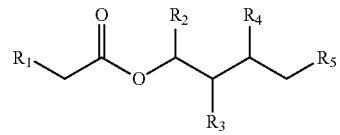

wherein $R_1$, $R_2$, $R_3$, $R_4$, and $R_5$ are each selected from a group consisting of hydrogen, a methyl group, an ethyl group, and a fluoroalkyl group.

The foregoing outlines features of several embodiments so that those of ordinary skill in the art may better understand the aspects of the present disclosure. Those of ordinary skill in the art should appreciate that they may readily use the present disclosure as a basis for designing or modifying other processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

What is claimed is:
1. A method for lithography patterning, comprising:
providing a substrate;
forming a material layer over the substrate;
exposing a portion of the material layer to a radiation; and
removing an unexposed portion of the material layer in a developer, resulting in a patterned material layer, wherein the developer contains an organic solvent having a Log P value greater than 1.82, wherein the material layer is a negative tone resist whose solubility in the developer decreases upon the radiation.
2. The method of claim 1, wherein the organic solvent is represented by the formula:

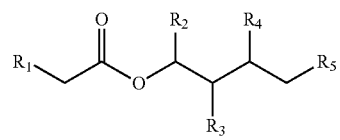

wherein $R_1$, $R_2$, $R_3$, $R_4$, and $R_5$ are each selected from a group consisting of hydrogen, a methyl group, an ethyl group, and a fluoroalkyl group; and wherein at least one of the $R_1$, $R_2$, $R_3$, $R_4$, and $R_5$ is not hydrogen.
3. The method of claim 2, wherein $R_1$, $R_2$, $R_3$, $R_4$, and $R_5$ are each a methyl group.

4. The method of claim 2, wherein $R_1$, $R_2$, $R_3$, $R_4$, and $R_5$ are each an ethyl group.

5. The method of claim 2, wherein $R_1$, $R_2$, $R_3$, $R_4$, and $R_5$ are each a fluoroalkyl group having $CF_3$.

6. The method of claim 2, wherein $R_1$, $R_2$, $R_3$, $R_4$, and $R_5$ are each a fluoroalkyl group having $C_2F_5$.

7. The method of claim 1, wherein the material layer contains more than 0% and less than 40% Polyhydroxystyrene (PHS).

8. The method of claim 1, wherein the radiation is an extreme ultraviolet (EUV) radiation.

9. The method of claim 1, wherein the radiation is an electron beam (e-beam).

10. The method of claim 1, wherein the developer further contains n-butyl acetate.

11. A method for lithography patterning, comprising:
    forming a resist layer over a substrate;
    exposing a portion of the resist layer to an EUV radiation; and
    removing an unexposed portion of the resist layer in a developer, resulting in a patterned resist layer, wherein the developer has a Log P value greater than 1.82 and contains a solvent that is an n-butyl acetate (n-BA) derivative.

12. The method of claim 11, wherein the solvent is represented by the formula:

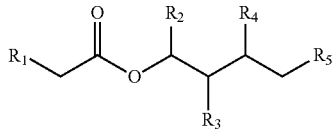

wherein $R_1$, $R_2$, $R_3$, $R_4$, and $R_5$ are each selected from a group consisting of hydrogen, a methyl group, an ethyl group, and a fluoroalkyl group.

13. The method of claim 11, the resist contains more than 0% and less than 40% Polyhydroxystyrene (PHS).

14. The method of claim 11, the resist contains about 5% photo acid generator.

15. The method of claim 14, further comprising, after the exposing of the portion of the resist layer and before the removing of the unexposed portion:
    performing a post-exposure bake to the resist layer.

16. The method of claim 11, wherein the developer further contains n-butyl acetate.

17. The method of claim 11, wherein the removing of the unexposed portion includes:
    applying the developer to the resist layer using a spin-on process.

18. A lithography developing composition with a Log P value greater than 1.82, comprising n-butyl acetate (n-BA) and an organic solvent that is represented by the formula:

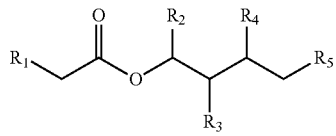

wherein $R_1$, $R_2$, $R_3$, $R_4$, and $R_5$ are each selected from a group consisting of hydrogen, a methyl group, an ethyl group, and a fluoroalkyl group; and wherein at least one of the $R_1$, $R_2$, $R_3$, $R_4$, and $R_5$ is not hydrogen.

19. The lithography developing composition of claim 18, wherein at least one of the $R_1$, $R_2$, $R_3$, $R_4$, and $R_5$ is a fluoroalkyl group having $CF_3$.

20. The lithography developing composition of claim 18, wherein at least one of the $R_1$, $R_2$, $R_3$, $R_4$, and $R_5$ is a fluoroalkyl group having $C_2F_5$.

* * * * *